(12) United States Patent
Quesada et al.

(10) Patent No.: US 10,513,842 B2
(45) Date of Patent: Dec. 24, 2019

(54) PORTABLE DIALYSIS DRAINAGE SYSTEM AND METHOD

(71) Applicants: Gene Quesada, Highland, CA (US); Roger Golightly, Nevada City, CA (US)

(72) Inventors: Gene Quesada, Highland, CA (US); Roger Golightly, Nevada City, CA (US)

(*) Notice: Subject to any disclaimer, the term of this patent is extended or adjusted under 35 U.S.C. 154(b) by 0 days.

(21) Appl. No.: 16/049,341

(22) Filed: Jul. 30, 2018

(65) Prior Publication Data

US 2019/0032320 A1 Jan. 31, 2019

Related U.S. Application Data

(60) Provisional application No. 62/539,030, filed on Jul. 31, 2017.

(51) Int. Cl.
| | | |
|---|---|---|
| *E03D 11/02* | (2006.01) | |
| *E03C 1/122* | (2006.01) | |
| *A61M 1/00* | (2006.01) | |
| *A61M 1/14* | (2006.01) | |
| *E03D 11/13* | (2006.01) | |

(52) U.S. Cl.
CPC ......... *E03D 11/025* (2013.01); *A61M 1/0021* (2013.01); *A61M 1/14* (2013.01); *E03C 1/1225* (2013.01); *E03D 11/13* (2013.01)

(58) Field of Classification Search
CPC ...................................................... E03D 11/25
USPC ............................................................. 4/420
See application file for complete search history.

(56) References Cited

U.S. PATENT DOCUMENTS

| 6,986,171 B1* | 1/2006 | Perrin ..................... E03D 11/12 |
| | | 4/300.2 |
| 10,151,093 B2* | 12/2018 | Quesada ............... E03D 11/025 |
| 2005/0001110 A1* | 1/2005 | Simon ..................... A61M 1/28 |
| | | 248/95 |
| 2019/0106872 A1* | 4/2019 | Grover .................... E03D 11/13 |

* cited by examiner

*Primary Examiner* — Christine J Skubinna
(74) *Attorney, Agent, or Firm* — Fulwider Patton LLP

(57) ABSTRACT

A toilet modified for disposal of dialysis waste includes a base, a bowl, a water supply port, and a dialysis drain port. In the dialysis drain port is a two piece air gap device that establishes a gap between ends of first and second drain tubes of a dialysis machine and a fluid level in the air gap. RO water and effluent from the dialysis machine enter the chamber of the air gap and mix, before being passed along a path from the dialysis drain port to the bowl of the toilet, where it can be dispelled in a sanitary manner in compliant with all pertinent codes and regulations.

3 Claims, 4 Drawing Sheets

PORTABLE DIALYSIS DRAINAGE SYSTEM AND METHOD

CROSS-REFERENCES TO RELATED APPLICATIONS

This application is a continuation in part of U.S. patent application Ser. No. 15/486,552, filed Apr. 13, 2017, and further claims priority to U.S. Provisional Patent Application No. 62/539,030, filed Jul. 31, 2017, the contents of which are fully incorporated by reference herein.

BACKGROUND

In humans, the kidneys have an important role in maintaining health. When healthy, the kidneys maintain the body's internal equilibrium of water and minerals (sodium, potassium, chloride, calcium, phosphorus, magnesium, sulfate). The acidic metabolism end-products that the body cannot get rid of via respiration are also excreted through the kidneys. The kidneys also function as a part of the endocrine system, producing erythropoietin, calcitriol and renin. Erythropoietin is involved in the production of red blood cells and calcitriol plays a role in bone formation.

Dialysis is a process for removing waste and excess water from a patient's blood, and is used in many cases where a patient has lost kidney function or suffer from kidney failure. Dialysis may be used for those with an acute disturbance in kidney function (acute kidney injury, previously acute renal failure) or progressive but chronically worsening kidney function—a state known as chronic kidney disease stage 5 (previously chronic renal failure or end-stage renal disease). The latter form may develop over months or years, but in contrast to acute kidney injury is not usually reversible and dialysis is regarded as a "holding measure" until a kidney transplant can be performed or sometimes as the only supportive measure in those for whom a transplant would be inappropriate.

Dialysis is an imperfect treatment to replace kidney function because it does not correct the compromised endocrine functions of the kidney. Dialysis treatments replace some of these functions through diffusion (waste removal) and ultrafiltration (fluid removal). To accomplish this, the dialysis machine mixes and monitors the dialysate. Dialysate is the fluid that helps remove the unwanted waste products from your blood. It also helps get a patient's electrolytes and minerals to their proper levels in your body. The machine also monitors the flow of blood while it is outside of the patient's body.

A typical dialysis machine uses one or more container that is used in the dialysis process. These containers hold the liquids used to mix the dialysate. The machine mixes the dialysate, which is made up of an acidified solution, bicarbonate and purified water. The acidified solution contains electrolytes and minerals, sometimes referred to by patients as "acid." The other solution is bicarbonate or bicarb, which is like baking soda. Both solutions are mixed inside the dialysis machine with purified water. While the patient is dialyzing, dialysate and blood flow through the dialyzer (through separate and unconnected paths). Fresh dialysate from the machine enters the dialyzer throughout the treatment. Impurities are filtered out of the patient's blood and into the dialysate. Dialysate containing unwanted waste products and excess electrolytes leave the dialyzer and are flushed into a waste receptacle.

The disposal of the product of the dialysis procedure is governed by various health codes. An example of a typical health code is Title 77 of the Illinois Health Code, Section 890.740, which states:

a) The water supply inlet to kidney dialysis equipment shall have a reduced pressure principle backflow preventer assembly complying with ASSE 1013 or a fixed air gap.

1) A portable dialysis unit or machine shall have a reduced pressure principle backflow preventer assembly installed on the water supply inlet on the unit.

2) Stationary dialysis equipment within a facility shall require, at the filter room or the dialysis machines, a reduced pressure principle backflow preventer assembly on the water supply or a water supply with a fixed air gap.

3) Dialysis equipment shall be installed in accordance with this Part and the manufacturer's specifications. Any conflicts shall be submitted to the Department for resolution.

b) The water supply to a dialysis reuse room or dialysis machine repair room shall be isolated from all other deionized (DI) or reverse osmosis (RO) water lines by an RPZ or an air gap.

c) A sign no smaller than 8 by 10 inches with the wording "This Water For Dialysis Only" shall be placed above a sink with DI water or RO water supplied to the faucet.

d) The discharge for each dialysis unit or machine, portable or stationary, shall be provided with an individual indirect waste connection to the sanitary drainage system. Each stand pipe shall be individually trapped and vented.

Each State has its own Plumbing Code, which is similar, and governing bodies include the Department of Public Health and the Office of Statewide Health Planning and Development. The issue with the disposal of the waste is that few hospital rooms or patient care facilities are equipped to comply with the last requirement of the health code cited above. That is, the requirement that each discharge shall be provided with an individual indirect waste connection to the sanitary drainage system. Thus, many hospitals and other patient care facilities do not comply with the health codes associated with dialysis byproduct waste. The art would benefit from an easy solution to this problem that brings the facility in compliance with the health codes in a reliable and safe manner.

The invention seeks to solve this dilemma. The invention converts any hospital or healthcare facility (or domestic) bathroom into a fully compliant portable dialysis compatible disposal system. Typically, non-compliant hospitals use as the water supply a make-shift cut in the valve under the sink, or a rubber hose attached to the goose neck of a faucet. Both of these items would need a small back flow check valve to make the systems code compliant. On the waste side, the dialysis byproduct is routed to the nearest drain or toilet in an "open" line, although the code requires an "air gap" which is often ignored.

SUMMARY OF THE INVENTION

The invention allows a simple but effective modification of a commercial toilet hook-up to be code compliant. To accomplish the modified toilet system, which can be original hardware or a kit to modify existing toilets, include a conduit leading from the toilet base to a passage way that leads to outlets on the rim of the bowl. This allows for the portable dialysis machine to drain the unused, byproducts of filtering RO water needed for the procedure and the effluent from the dialysis treatment directly into the toilet/sewer system. The invention accommodates approximately 6 to 7.5 gallons a minute, and connects directly to the toilet at the conduit.

Currently, these drain lines are being dumped into shower drains and, in some cases, sink drains or the toilet bowl directly. This is very unsanitary. This current situation is being overlooked by the regulatory agencies due to the high volume of portable dialysis needed in a hospital setting. To accommodate the codes for drainage, the conduit seats an air gap device to ensure no waste enters the water supply system.

The present invention requires no significant changes to the layout of the bathroom, such as opening up walls and running new waste lines, supply lines, primer traps and specialized dialysis boxes, which could cost many thousands of dollars to effect for each bathroom and would take the bathroom out of service for the duration of the repair. Conversely, the present invention can be installed in a single day or less with multiple rooms done in the same time frame given the crew size and the patient/patients would not necessarily need to be moved. With the retrofit in an existing building, there is no need to install infection barriers, negative air set up or any other needed items for a construction related project.

In most cases the present invention is considered a repair (but in some cases may require an OSHPD permit), requiring no special permits by Statewide Health Planning and Development, or other governing bodies for all construction work done in a hospital setting. The invention involves adding a conduit adjacent the toilet water supply, whether the toilet is wall mounted or floor mounted. This allows for a portable dialysis machine to drain the unused, byproducts of filtering RO water needed for the procedure and the waste from the dialysis treatment, via two tubes, into the conduit at the air gap device to convey the waste directly into the toilet's sewer system. Dumping the byproducts directly into a toilet is found to be the best way to dispose of these byproduct.

These, and other benefits of the present invention, will best be understood with reference to the accompanying figures and the discussion in the detailed description of the invention set forth below.

DETAILED DESCRIPTION OF THE PREFERRED EMBODIMENTS

It is required by building codes that dialysis water treatment equipment be connected to a source of water through a backflow prevention device (also known as a reverse flow prevention device). The purpose of this is to prevent water from the water treatment equipment being pulled backward through the building's water supply piping. The backflow prevention device prevents the draining back of water from the treatment system. The backflow prevention device also prevents the backflow of chemicals into the building water main during the process of chemical disinfection of the water treatment system, thus eliminating the risk of chemical exposure to the other parts of the building. That is, if the system was being disinfected, the chemical would be pulled into the water main as well.

Figure 1:
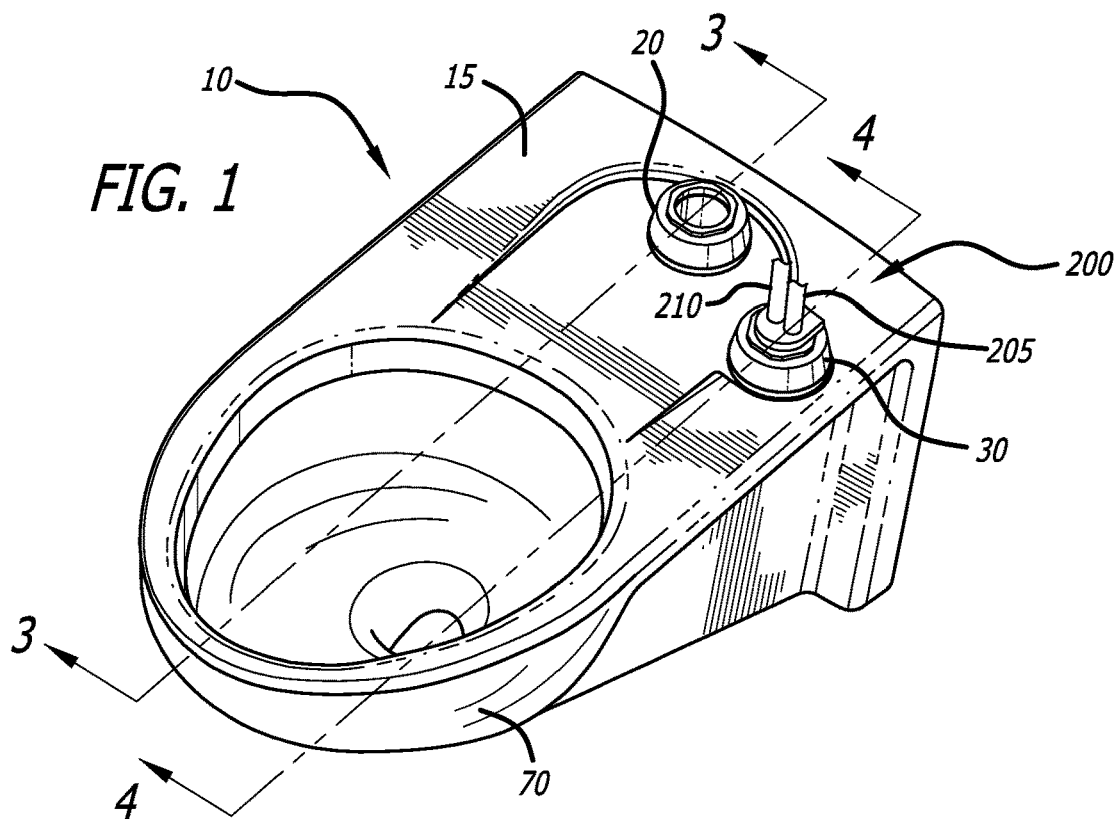
FIG. 1 is an elevated, perspective view of a first preferred embodiment of the present invention.
Figure 2:
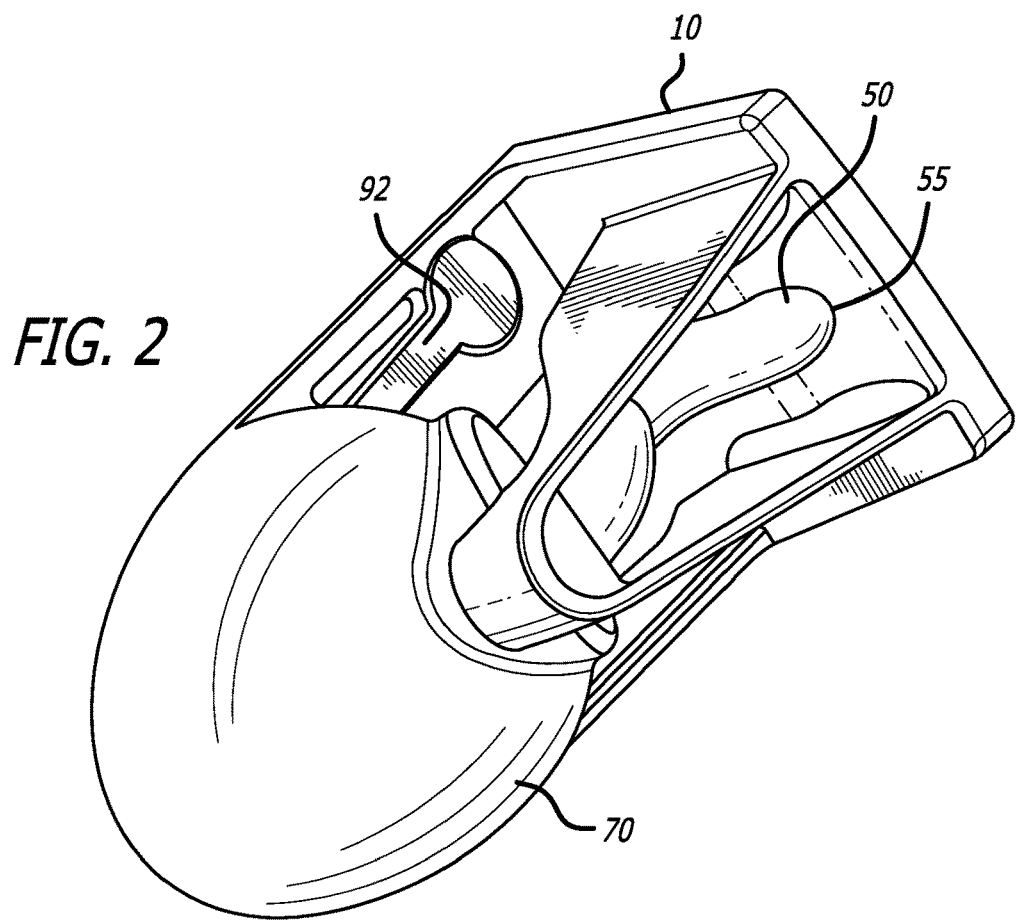
FIG. 2 is an elevated, perspective view of the embodiment of FIG. 1 from below.
Figure 5:
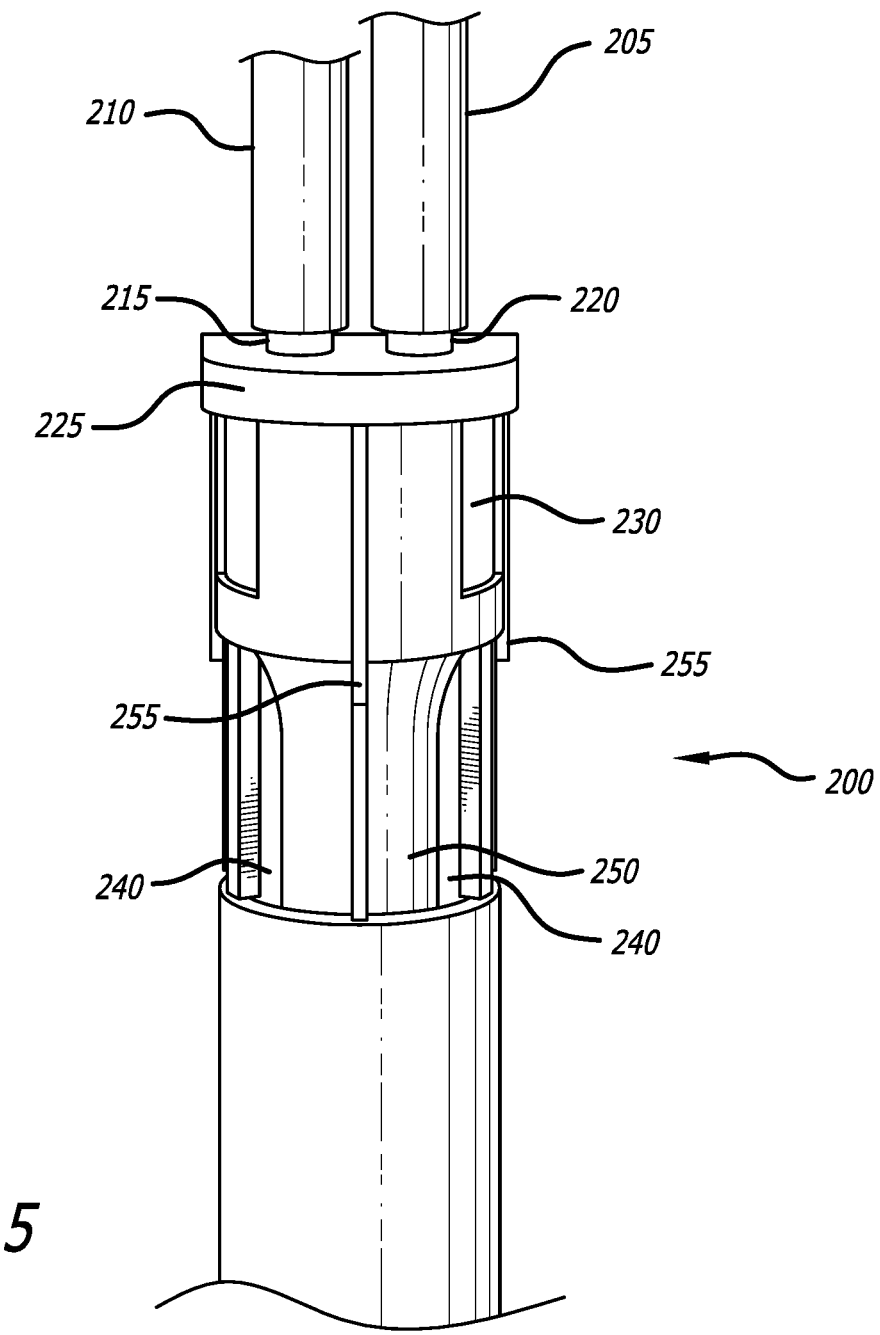
FIG. 5 is an elevated perspective view of an air gap device inserted into the conduit of FIG. 1.

A toilet having the features of the present invention is generally illustrated in FIGS. 1-2. The toilet 10 includes a base 15 and a bowl 70, and a water supply port 20 that receives water from a water source (not shown) as is customary. FIG. 1 also depicts a second port or conduit 30 adjacent the water supply port 20, where the byproducts of a dialysis procedure can be directly drained to the toilet 10. Inserted releasably into the conduit 30 is an air gap device, shown in more detail in FIG. 5. The air gap device 200 receives tubes 205,210 from the dialysis machine carrying effluent and RO water from the dialysis system. The tubes 205, 210 are fitted onto stems 215, 220 mounted on the cover 225, and the stems have inlets to direct the fluid into a chamber within the air gap device. The chamber includes windows 230 that allow fluid backing up from the toilet out of the air gap device so that if the fluid level rises to the window it will spill out before it returns to the tubes 205, 210. The chamber funnels to the inlet of the conduit 30, and the air gap device 200 has a narrow exit 250 with a diameter smaller than the diameter of the conduit 30. Ribs 255 define backflow channels 240 such that fluid back flow from the conduit will overflow the conduit 30 at the channels 240 before entering the chamber of the air gap device, preventing return of the waste and effluent into the dialysis system.

Figure 3:
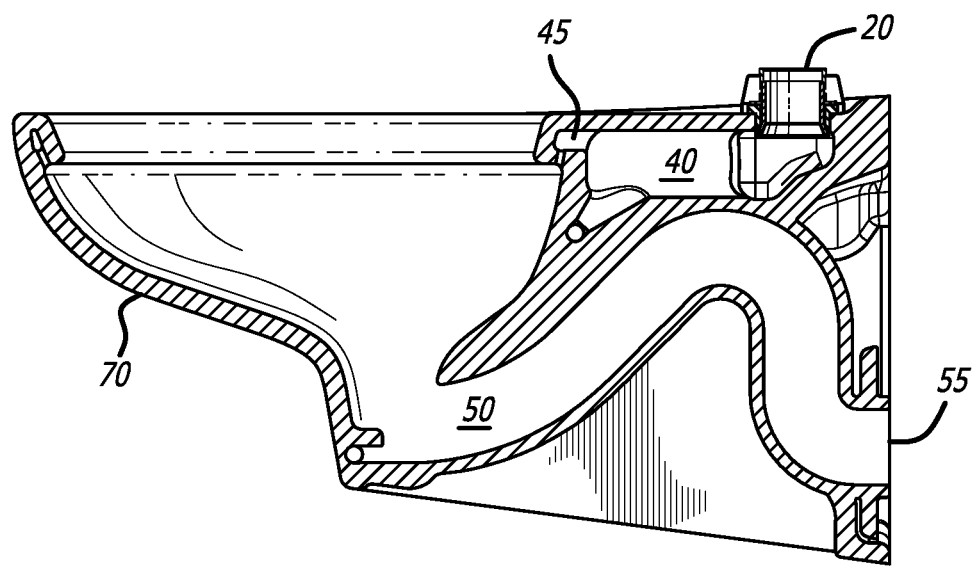
FIG. 3 is a cross sectional view of the toilet of FIG. 1 taken along line 3-3.

FIG. 3 illustrates the toilet and the port 20 for the water supply to help evacuate waste from the toilet 10. Water enters the port 20 and collects in a reservoir 40, before being released through a vortex inducing exit port at the upper rim of the bowl 70. The water and waste drain through the passage 50 and exit to a sewage line connected to outlet 55.

Figure 4:
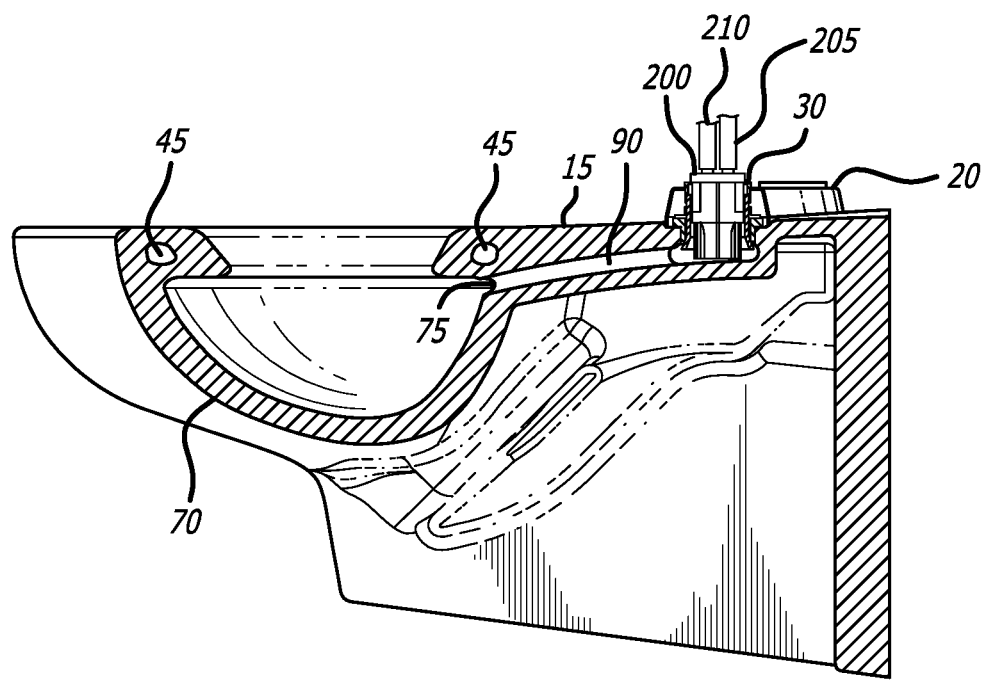
FIG. 4 is a cross sectional view of the toilet of FIG. 1 taken along line 4-4.

FIG. 4 illustrates the disposal pathway for the byproduct of the dialysis procedure. The RO water and effluent from the dialysis machine enter the air gap device 200 at conduit 30. The liquids mix in the air gap device before exiting the air gap device into a passage 90 formed inside a channel 92 on the underside of the base 15 of the toilet 10. The waste fluids flow gravitationally downward through the passage 90 and are released into the bowl 70 at outlet 75, where they circle the bowl and are evacuated when the toilet is flushed along with the water and any other waste. The backflow prevention device, or air gap device 200, prevents any of the contents in the passage 90 flowing back up into the RO water supply or the waste tube, as the fluid would spill out of the air gap device before it reached to tubes 205, 210.

Figure 6:
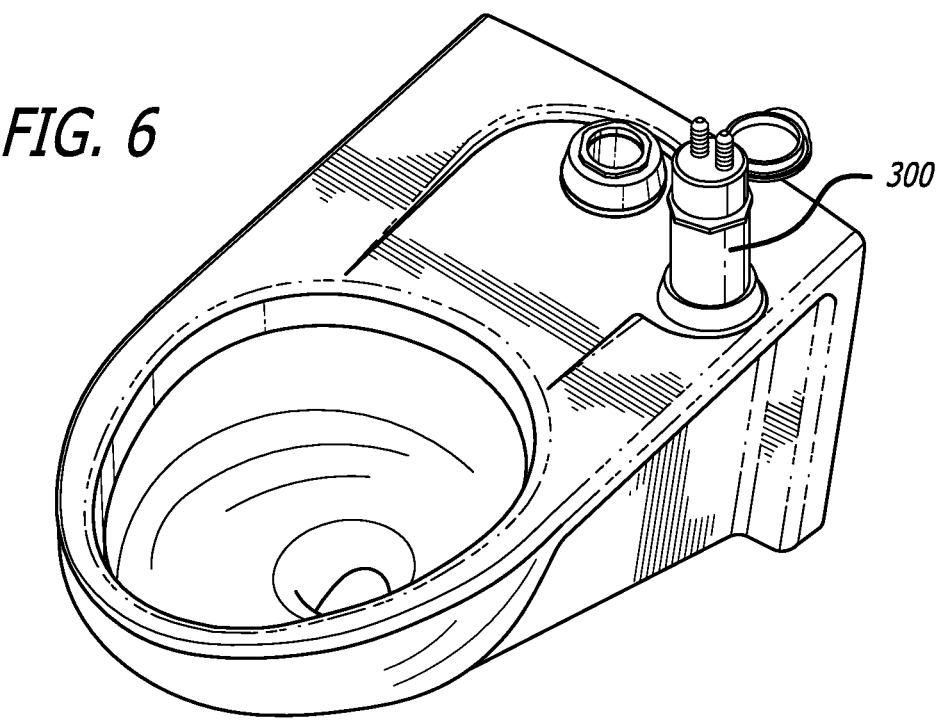
FIG. 6 is an elevated, perspective view of a toilet with an alternate two piece air gap device.
Figure 7:
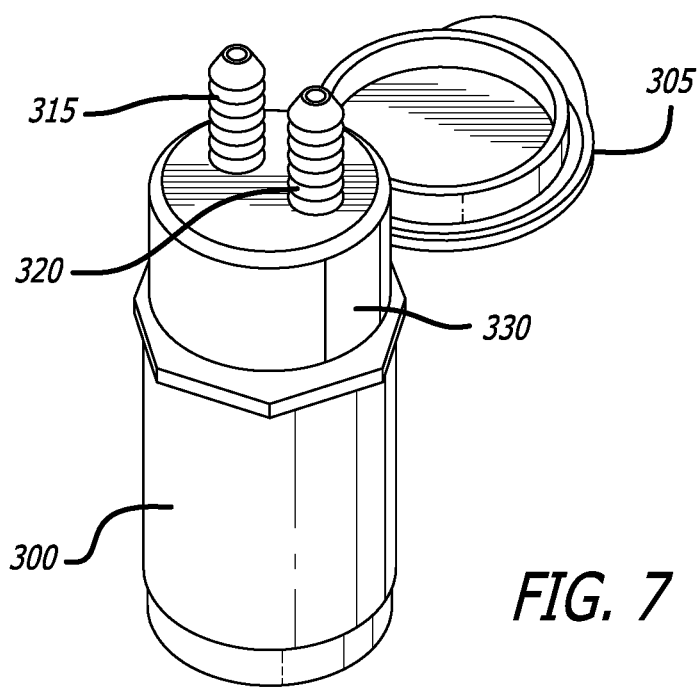
FIG. 7 is an enlarged perspective view of the alternate two piece air gap device.

FIG. 6 depicts a toilet with an alternate two piece air gap device 300. The air gap device 300, shown in more detail in FIG. 7, includes stems 315, 320 and a window 330, but further includes a cap 305 for enclosing the connector when not in use. The air gap connects to the water/waste inlet 30 and the dual stems connect with ⅜ inch ID tubing. The RO water and effluent from the dialysis machine enter the air gap 300 at conduit 30, and the liquids mix in passage way 92 and bowl 70 of the toilet 70. The waste fluids flow gravitationally downward through the passage 90 and are released into the bowl 70 at outlet 75 as discussed previously. The two piece air gap device 300 prevents any of the contents of the passage 90 flowing back up into the RO water supply or the waste tube, as the backflow would evacuate through the window before it reached the tubes 205, 210.

The connector includes a specially designed air gap permits rapid and safe disposal of the dialysate and the waste water from reverse osmosis filtration in a code compliant manor into the toilet directly. California Building Code Chapter 8, INDIRECT WASTES, 801.0 & 801.1 covers the Air Gap requirements enforced by OSHPD in California for Hospitals settings and is also enforced in all counties by local construction authorities overseeing constructions projects in commercial and residential plumbing applications in the state of California. The air gap of FIG. 7, which is mold injected and made out a moldable plastic such as Polypropylene, work with the fixture of FIG. 4 to communicate the waste into the bowl. The air gap height may vary due to water flow calculations, but the flow rates are estimated to be in the range of 6-7.5 gallons per hour.

While the inventors' preferred embodiments of the present invention have been described and depicted in the foregoing descriptions and accompanying drawings, it is to be understood that one of ordinary skill in the art would readily appreciate that certain modifications and substitutions can be made to the embodiments described and depicted herein. Further, it is intended by the inventors that the present invention include all such modifications and substitutions. Accordingly, the present invention is not limited to any particular embodiment described herein unless expressly so limited, and that the scope of the invention is properly interpreted by the words of the appended claims using their customary and ordinary meanings.

We claim:

1. A toilet modified for disposal of dialysis waste, comprising: a base;
   a bowl;
   a water supply port;
   a dialysis drain port;
   two piece air gap device having first and second stems affixed to the first part, a window in the first part, and a cap for closing the two piece air gap when not in use, where RO water and effluent from a dialysis operation enter the two piece air gap at the respective first and second stems, the two piece air gap device adapted to prevent any fluids from flowing back up into the first and second stems by evacuating said fluids through the window before the fluids reach the first and second stems; and
   a path from the dialysis drain port to the bowl of the toilet.

2. The toilet of claim 1, wherein the path from the dialysis drain port to the bowl of the toilet induces a vortex in the resulting stream.

3. The toilet of claim 1, wherein the RO water and effluent from the dialysis machine mix in the two piece air gap device prior to entering the path from the dialysis drain port to the bowl.

* * * * *